(12) United States Patent
Cunningham et al.

(10) Patent No.: US 6,805,839 B2
(45) Date of Patent: Oct. 19, 2004

(54) RESPONSE MICROCANTILEVER THERMAL DETECTOR

(76) Inventors: Joseph P. Cunningham, 975 W. Outer Dr., Oak Ridge, TN (US) 37830; Slobodan Rajic, 1006 Royal Mew Ct., Knoxville, TN (US) 37922; Panagiotis G. Datskos, 8444 Mecklenburg Ct., Knoxville, TN (US) 37923; Boyd M. Evans, III, 949 W. Outer Dr., Oak Ridge, TN (US) 37830

(*) Notice: Subject to any disclaimer, the term of this patent is extended or adjusted under 35 U.S.C. 154(b) by 356 days.

(21) Appl. No.: 09/811,234

(22) Filed: Mar. 16, 2001

(65) Prior Publication Data
US 2001/0020680 A1 Sep. 13, 2001

Related U.S. Application Data

(63) Continuation-in-part of application No. 09/267,292, filed on Mar. 12, 1999.
(60) Provisional application No. 60/192,910, filed on Mar. 29, 2000.

(51) Int. Cl.$^7$ .................. G01N 15/06; G01N 33/00; G01N 33/48; G01N 25/00; G01N 25/20
(52) U.S. Cl. .............. 422/82.12; 422/68.1; 422/50; 422/51; 422/57; 422/83; 436/147; 73/23.2; 73/25.01; 374/100; 374/130
(58) Field of Search ................ 422/68.1, 57, 51, 422/50, 82.12, 83; 436/147; 356/328; 374/100, 130; 73/23.2, 25.01

(56) References Cited

U.S. PATENT DOCUMENTS

| 5,763,782 | A | | 6/1998 | Moore et al. |
| 5,908,981 | A | | 6/1999 | Atalar et al. |
| 5,923,421 | A | * | 7/1999 | Rajic et al. ................. 356/328 |
| 5,965,886 | A | | 10/1999 | Sauer et al. |
| 6,096,559 | A | * | 8/2000 | Thundat et al. ............. 436/147 |
| 6,436,346 | B1 | * | 8/2002 | Doktycz et al. .............. 422/51 |

OTHER PUBLICATIONS

Evans, B.M., III et al., "Optimization of Micromechanical Photon Devices," SPIE's International Symposium SPIE–The International Society of Optical Engineering (Bellingham, WA), p. vol. 3778, (Jul. 18, 1999).

* cited by examiner

Primary Examiner—Jill Warden
Assistant Examiner—Brian Sines
(74) Attorney, Agent, or Firm—Kirk A. Wilson

(57) ABSTRACT

A "folded leg" thermal detector microcantilever constructed of a substrate with at least one leg interposed between a fixed end and a deflective end, each leg having at least three essentially parallel leg segments interconnected on alternate opposing ends and aligned in a serpentine pattern with only the first leg segment attached to the fixed end and only the last leg segment attached to the deflective end. Alternate leg segment are coated on the pentalever with coating applied to the top of the first, third, and fifth leg segments of each leg and to the bottom of the second and fourth leg segments of each leg.

19 Claims, 10 Drawing Sheets

(5 of 10 Drawing Sheet(s) Filed in Color)

RESPONSE MICROCANTILEVER THERMAL DETECTOR

CROSS REFERENCES TO RELATED APPLICATIONS

This application is a continuation-in-part of U.S. patent application Ser. No. 09/267,292, filed Mar. 12, 1999, and also claims priority to U.S. Provisional Patent Application No. 60/192,910, filed Mar. 29, 2000, all incorporated herein by reference.

STATEMENT REGARDING FEDERAL SPONSORSHIP

This invention was made with Government support under contract no. DE-AC05-00OR22725 to UT-Battelle, LLC, awarded by the United States Department of Energy. The Government has certain rights in the invention.

BACKGROUND OF THE INVENTION

The desire to shrink the size of mechanical components, optical devices, and sensors to sizes obtained by the microelectronics industry has driven a significant amount of research in the field of micro-electro-mechanical systems (MEMS). Micromechanical devices are currently being considered for a wide variety of applications including uncooled infrared detectors, micro-actuators, chemical detectors, and completed mechanical systems. Currently the dominant manufacturing method for micro-devices is the microlithography approach used by the microelectronics industry. This approach works well for producing a large quantity of devices, however the ability to produce prototype devices is not as developed as the ability to mass-produce devices. The ability to simulate the response of micro-devices using finite element analysis (FEA) gives researchers insight into the behavior of devices before prototypes are developed or production runs occur as well as allowing the designer to optimize the desired response.

Photon detectors represent a class of MEMS devices that have been studied with great interest. Several different types of photon detectors are available including CCDs, microbolometers, thermopiles and pyroelectrics. Solid state infrared detectors must be operated at reduced temperatures from the ambient in order to reduce thermal noise. The infrared thermal detectors in this invention convert the incident radiation into heat which produces a change in the position of the micro-cantilever through bimetallic bending or other effects. The effects of several design variables on the bending of microcantilever structures is necessary for development of an improved response detector.

BRIEF SUMMARY OF THE INVENTION

A "folded-leg" microcantilever thermal detector was fabricated using focused ion beam milling. This device was created as a compact, sensitive, thermal detector. A large collecting area (pad) was defined at the deflective end of a folded leg structure to maximize the energy absorbed. The purpose of folding the legs five times was to create a compact device that behaved thermally and mechanically as a larger device. The device with the legs folded five times is referred to as a pentalever. The collecting area is also the area used for optically measuring the displacement. The microcantilever detector was constructed of substrate having an upper side, lower side, fixed end, and deflective end, with the substrate having at least one leg interposed between the fixed end and the deflective end. Each leg has at least three essentially parallel leg segments interconnected on alternate opposing ends and aligned in a serpentine pattern with only the first leg segment attached to the fixed end and only the last leg segment attached to the deflective end. The preferred embodiment of the instant invention alternated leg segment coatings on the pentalever with coating applied to the top of the first, third, and fifth segments of each leg and to the bottom of the second and fourth leg segments. The deflective end may be coated or uncoated on the top and bottom.

BRIEF DESCRIPTION OF THE DRAWINGS

The file of this patent contains at least one drawing executed in color. Copies of this patent with color drawing(s) will be provided by the Patent and Trademark Office upon request and payment of necessary fee.

DETAILED DESCRIPTION

Figure 1:
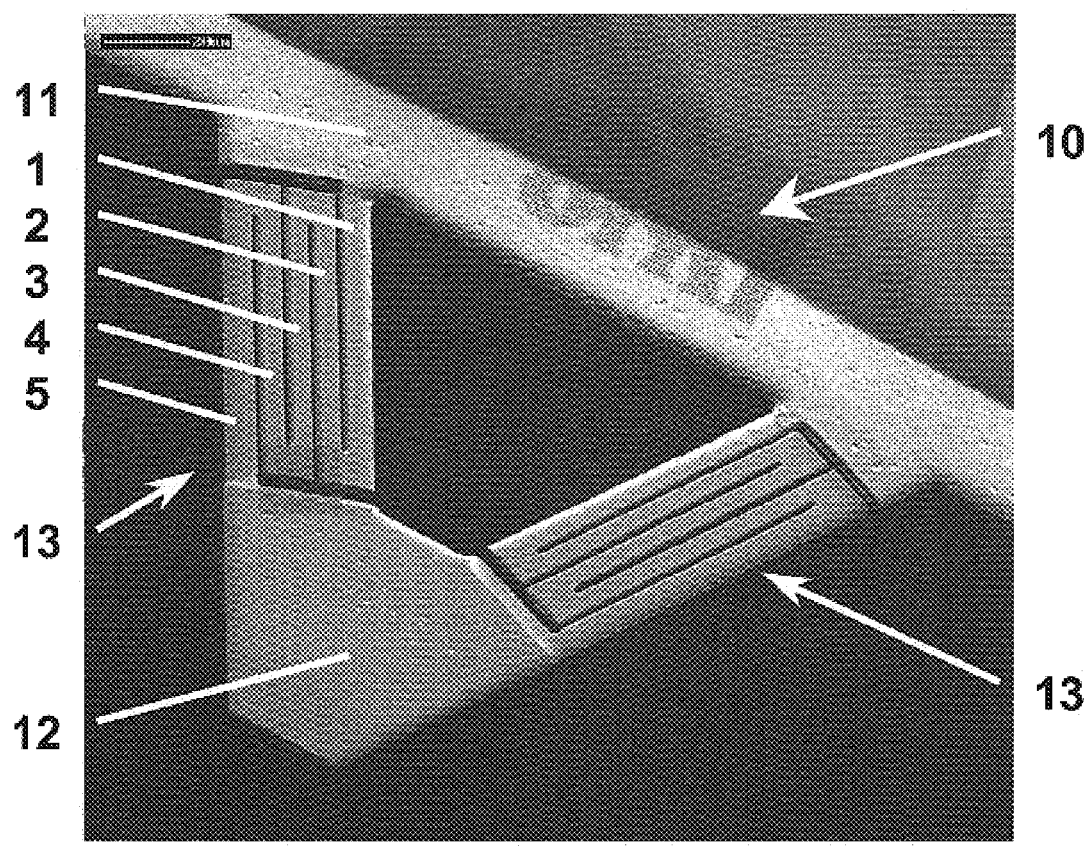
FIG. 1 is the five-leg segment micro-cantilever (pentalever) thermal detector of the instant invention.

Presently, there are a number of families of commercially available IR detectors, including thermopiles, bolometers, pyroelectrics, and various solid-state detectors. In this invention, we employed inexpensive micromechanical IR thermal detectors, which are based on the bending of a microcantilever as a result of absorption of IR energy. When a microcantilever is exposed to IR radiation, its temperature rises due to absorption of this energy.

Bimaterial microcantilevers are constructed from materials exhibiting dissimilar thermal expansion properties. For example, microcantilevers made from silicon nitride (or silicon) coated with a thin film of gold or platinum will exhibit the bimaterial effect. The bimaterial effect causes the microcantilever to bend in response to temperature variations. The extent of bending is directly proportional to the radiation intensity. Previous work has shown that microcantilever bending can be detected with extremely high sensitivity. For example, metal-coated microcantilevers that are commonly employed in atomic force microscopy (AFM) allow sub-Angstrom (<$10^{-10}$ m) sensitivity to be routinely obtained. Recent studies have reported the use of microcantilever bending for calorimetric detection of chemical reactions with energies as low as a few picoJoules. It was demonstrated that a similar microcantilever thermal detector had an observed sensitivity of 100 pW corresponding to an energy of 150 femtojoules and use of the sensor as a femtojoule calorimeter was proposed. An estimate of the minimum detectable power level was on the order of 10 pW, corresponding to a detectable energy of 10 fJ and a temperature sensitivity $10^{-5}$ K. However, using an optimally designed microcantilever, the sensitivity may be improved even further.

The bending of a rectangular bimaterial microcantilever is proportional to the absorbed energy. The maximum deflection, $z_{max}$, due to differential stress is given by:

$$z_{max} = \frac{5}{4} \frac{(t_1+t_2)l^3}{(\kappa_1 t_1 + \kappa_2 t_2)wt_2^3} \times \frac{(\alpha_1 - \alpha_2)}{2 + 6\frac{t_1}{t_2} + 6\frac{t_1^2}{t_2^2} + \frac{E_1}{E_2}\frac{t_1^3}{t_2^3} + \frac{E_2}{E_1}\frac{t_2}{t_1}} \times \eta\left(\frac{dQ}{dt}\right)$$

where l and w are, the length and width of the microcantilever, respectively, $t_1$ and $t_2$ are the thickness of the two layers, $\kappa_1$, $\kappa_2$, $\alpha_1$, $\alpha_2$, $E_1$, $E_2$ are the thermal conductivities; thermal expansion coefficients, and modulus of elasticity of the two layers, and $\eta dQ/dt$ is the fraction of the IR radiation power absorbed. In order to increase the IR detection sensitivity of a microcantilever, $z_{max}$ should be maximized. Note that $z_{max}$ and is strongly dependent on the geometry and thermal properties of the two layers.

A finite element analysis (FEA) model of the microdevice was developed in Pro/Mechanica consisting of 804 two-dimensional shell elements and 1,120 three-dimensional solid elements. The 804 two-dimensional shell elements were used to represent a thin layer of gold on the top of the triangular-shaped cantilever, and the solid elements were used to represent the silicon material in the triangular shaped cantilever and heat sink. The gold layer had a nominal thickness of 50 nanometers, and the cantilever itself had a thickness of 1 micrometer. The base of the triangular shaped cantilever was 200 micrometers and the height was 160 micrometers. The microstructure consists of a large absorbing area near the tip. The legs of the cantilever are folded five times before they attach to the heat sink in order to increase the thermal resistance of the system.

A steady-state analysis was performed on the model using conditions similar to those seen during laboratory experiments with a similar structure. A heat load was applied to the surface of the cantilever equivalent to 0.1 μW. The starting temperature of the structure was set to be 0° Centigrade in order to reduce any errors due to round-off or division by very small numbers. Setting the starting temperature at 0° C. also allows the results to represent the change in temperature. The heat loads were used in a thermal analysis to calculate the deflections caused by the incident, radiant energy. The temperature changes were transferred to the structural analysis and used to calculate the thermal deflection.

A modal analysis was performed to calculate the first four fundamental frequencies of the micro-device. Results of this analysis are used to gain insight into the potential response of the device. Convergence of 10 percent was achieved on all results.

An optimization study was performed to determine the effects of the bimaterial coating thickness on the maximum temperature change and the maximum deflection. In the optimization study, the thickness of the gold coating was varied from 50 nm to 500 nm. The analysis was performed to determine the effect of thickness on the maximum temperature change in the cantilever surface and the effect of coating thickness on the maximum temperature obtained by the cantilever. The 200 μm wide by 160 μm long cantilever was attached to a silicon "heat sink" that was 500 μm wide, 200 μm thick, and 200 μm deep. The bottom surface of the heat sink was constrained thermally to be 0° C. and was constrained structurally from all displacements.

To further improve thermal sensitivity, a change was made in the way the coating was simulated. Instead of simulating the entire top surface of the detector as having a gold coating, the coating was applied to the top of the first, third, and fifth folds of the legs, as well as the entire top of the collecting surface. The coating was then applied to the bottom surfaces of the second and fourth folds of the legs, as well as the entire bottom surface of the collecting area. The coating was simulated on both sides of the collecting surface in order to minimize the distortions in this surface. Distortions in the collecting surface result in an optical power or "lensing effect" and make optical measurement of deflections more difficult.

The pentalever 10 detector of this invention, as shown in FIG. 1, was constructed of substrate having an upper side (shown), lower side (hidden), fixed end 11, and deflective end 12, with the substrate having at least one leg 13 interposed between the fixed end and the deflective end. Each leg has five essentially parallel leg segments 1, 2, 3, 4, 5 interconnected on alternate opposing ends and aligned in a serpentine pattern with only the first leg segment 1 attached to the fixed end 11 and only the last leg segment 5 attached to the deflective end 12.

Figure 2:
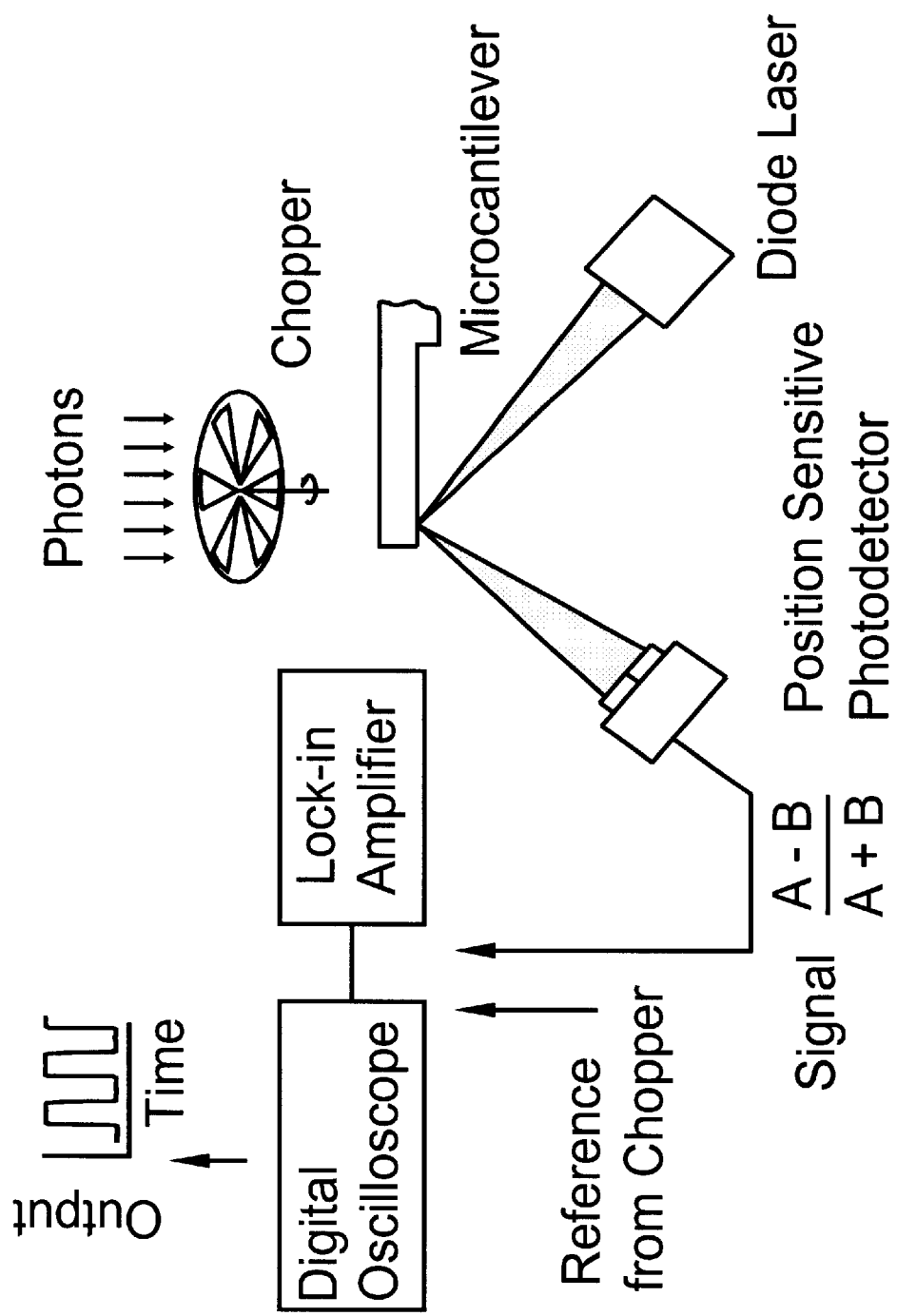
FIG. 2 is the experimental measurement setup used for testing microcantilevers.

The response of our devices using the experimental setup shown in FIG. 2 was recorded. To detect movement of the cantilever, a diode laser (delivering 1 mW at 670 nm) was focused on the tip of the microcantilever using a 20-power microscope objective. In order to minimize heating of the tip by the probe laser, optical power was reduced by placing a neutral density filter with an optical density of 1.0 between the probe laser and the objective. A quad-element (A,B,C,D) photodiode detector was used to collect the reflected probe beam. The current output $(i_{A,B,C,D})$ of the photodiode depends linearly on the bending of the microcantilever. A high, narrow bandpass optical filter was placed in front of the photodiode allowing the laser beam to be detected while preventing other wavelengths from reaching the photodiode. The amplified differential current signal from the quad cell photodiode, $i_{A,B,C,D}$ $[=(i_A+i_B)-(i_C+i_D)/(i_A+i_B+i_C+i_D)]$, was monitored and recorded using a digital oscilloscope (TDS 780, Tektronix) or sent to a lock-in amplifier (SR850, Stanford Research Systems) for signal extraction and averaging.

The cantilevers used for this experiment were triangular silicon pentalevers and two different designs were studied. The first design was 1.0 μm thick and had a 50 nm thick gold/chromium film uniformly covering one side. A modified version of the first design was studied which was 1 μm thick and had the gold coating applied to the entire front and back surface of the detector "pad" area and alternated on the front and back of the folded legs. Optical read-out was used to measure the bending of the microcantilever thermal detector. Since the quad element photodiode was blind to IR, no additional filtering was needed for the read-out circuit.

Modal analysis was performed to determine the first four fundamental frequencies of the device. The results of the modal analysis are shown in Table 1.

TABLE 1

Micro-device natural frequencies.

| Mode | Frequency (kHz) |
|---|---|
| 1 | 12.72 |
| 2 | 41.23 |
| 3 | 47.41 |
| 4 | 84.88 |

The analysis of the mode shapes gives insight into the potential dynamic response of the device, as well as the potential motion of the device during excitation.

Figure 10:
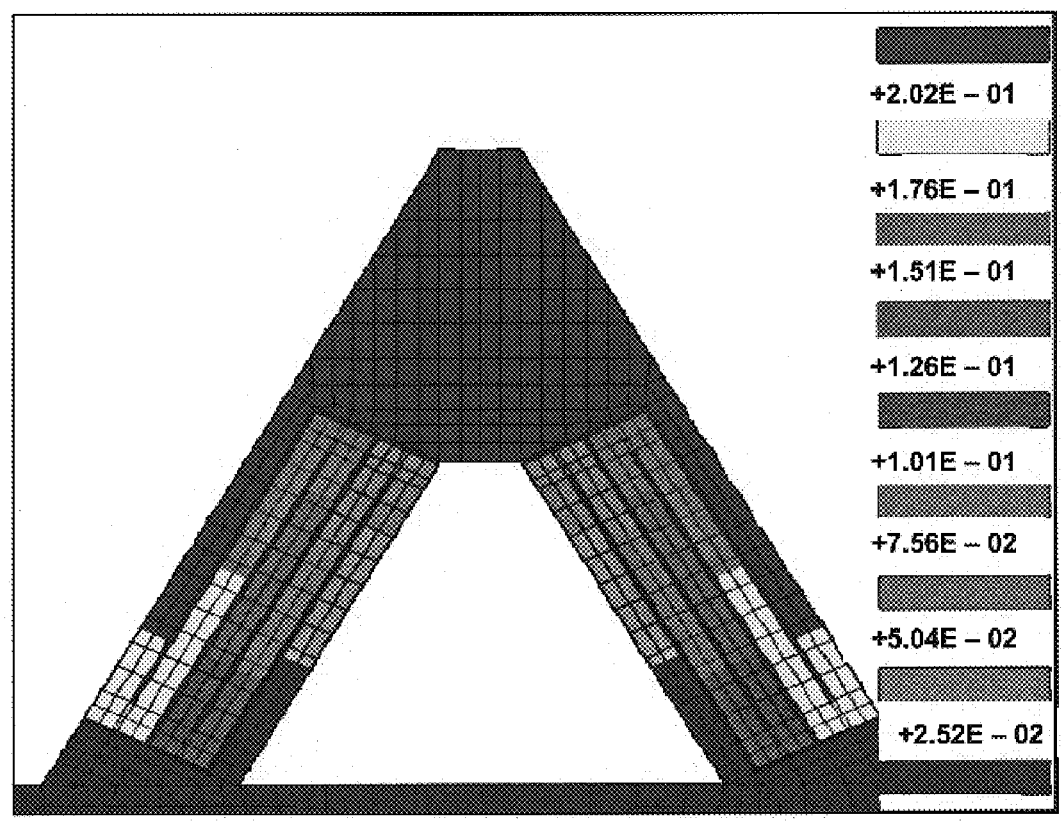
FIG. 10 shows the temperature distribution of the cantilever under a 1 $\mu$W heat load.

The thermal response of the cantilever with a uniform bimetallic coating on a single side to a 1 $\mu$W heat load is shown by the temperature distribution in FIG. 10. The energy flow from the pad area at the tip through the folded leg geometry is apparent. The temperature change along the path goes from greater than 0.2° C. to less than 0.02° C. as the thermal energy flows from the pad area to the heat sink. The maximum temperature change in the model when subjected to the 1 $\mu$W heat load was 0.23° C.

Figure 8:
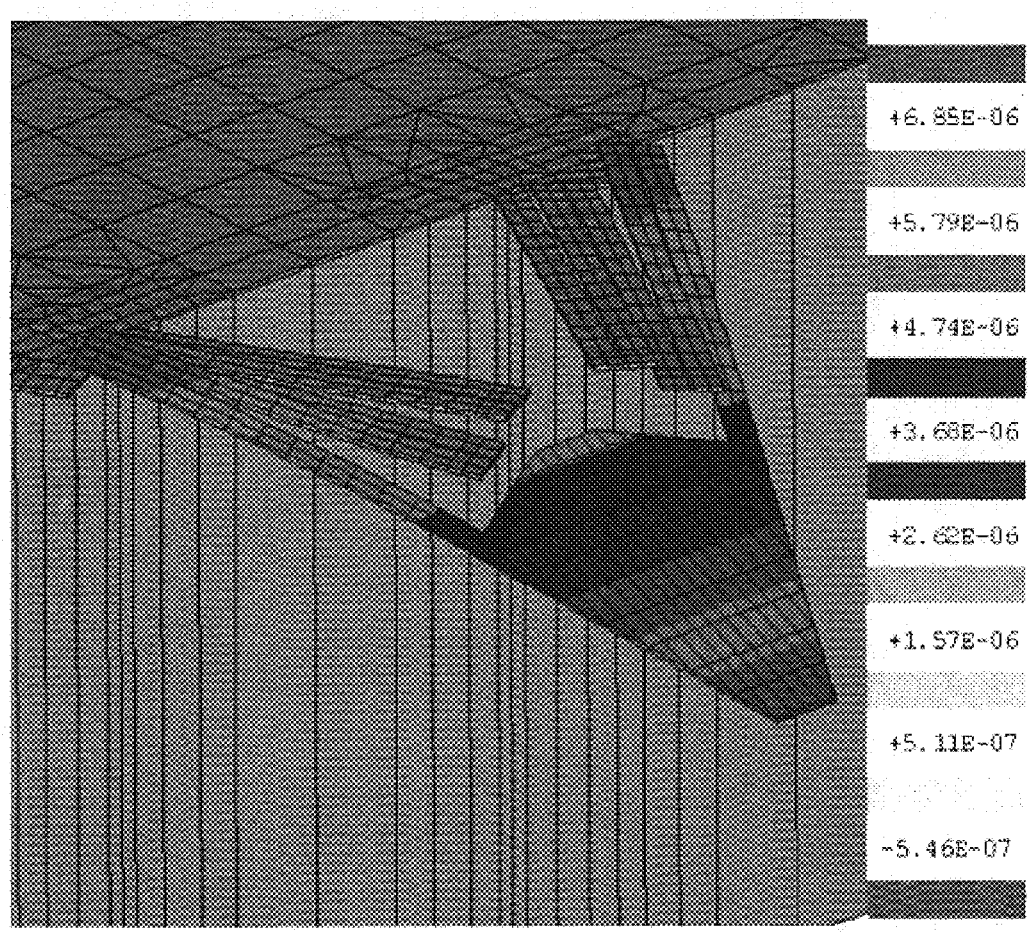
FIG. 8 is the FEA deflection results of alternating bimetallic-coated leg segment pentalever of the instant invention.

FIG. 8 shows the thermal bending under a 1 $\mu$W heat load of the folded leg cantilever with alternating leg segment coating of this invention. The maximum displacement due to bimetallic bending was 7.91 nm.

Figure 9:
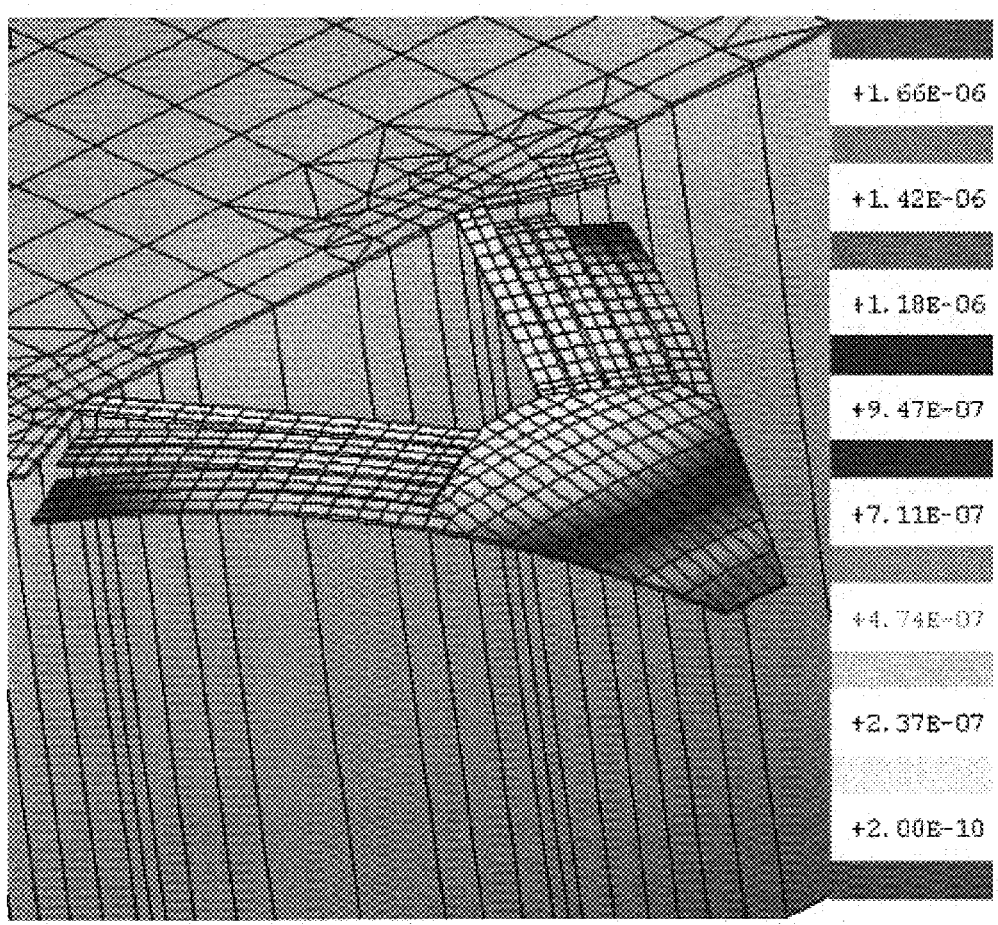
FIG. 9 is the FEA deflection results of a pentalever with a uniform bimetallic coating on a single side.

FIG. 9 shows the thermal bending under a 1 $\mu$W heat load of the folded leg cantilever with a uniform bimetallic coating on a single side. The maximum displacement due to bimetallic bending was 1.86 nm.

Optimization studies were performed to predict the tip displacement of the cantilever as a function of energy and to determine the effects of increasing the coating thickness on the displacement of the cantilever. Our results show that the effect of energy on the displacement of the cantilever tip were linear.

Figure 3:
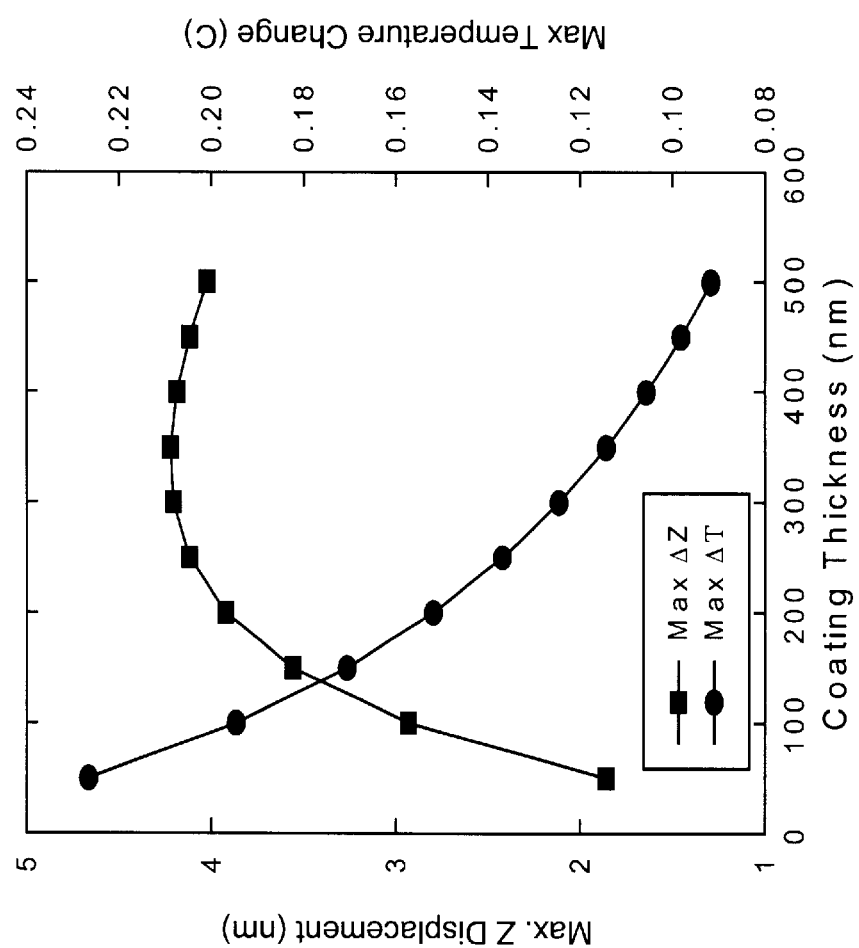
FIG. 3 is a graph of displacement and temperature change versus coating thickness.

Increasing the coating thickness resulted in a decrease in the maximum temperature change achieved in the cantilever. Due to an increase in the bimetallic effect with increased coating thickness, the bending increased to a maximum and then dropped off. The decrease in bending at the greatest coating thickness was due to the overall decrease in thermal resistance. The results of the optimization study are shown in FIG. 3, which plots maximum deflection and maximum temperature as a function of coating thickness.

A steady-state thermal analysis was performed on the cantilever model with the simulated coating applied to alternating legs and both sides of the sensing pad area. For the 1 $\mu$W heat load the alternating coating geometry experienced a maximum displacement 7.91 nm as opposed to 1.86 nm for the original geometry. These results agree well with preliminary experimental results that show a factor of three improvement in response by alternating the coating. Due to the larger gold-coated area on the alternating coating geometry, the maximum temperature change was 0.226° C. as opposed to 0.265° C. for the original geometry.

Another interesting effect of alternating the coating on the folded leg geometry and coating both sides of the collecting area was that more of a pure rotation of the collector area occurred. The rotation of elements in the center of the collector area was 0.0041° compared to 0.0013° for the device coated entirely on the front surface. The difference in the amount of warping of the collector surface is seen by comparing FIGS. 8 and 9.

In order to optimize the thermal detectors used in our micro-spectroscopy techniques, the response of microcantilevers to IR radiation was measured. A HeNe laser was used to thermally excite gold-coated microcantilevers. The bending of the microcantilever was determined using an optical read-out scheme as described earlier. The signal was digitized and stored, or sent to a lock-in amplifier. Assuming a uniform heat dissipation over the entire length, l, of the microcantilever (of thickness t) the change in temperature at the tip, $\Delta T(\approx l^2/2\lambda t \, dQ/dt)$, depends on geometry factors such as l and t. A temperature change of $\Delta T=10^{-4}$ K leads to deflections of approximately 1 nm.

Figure 5:
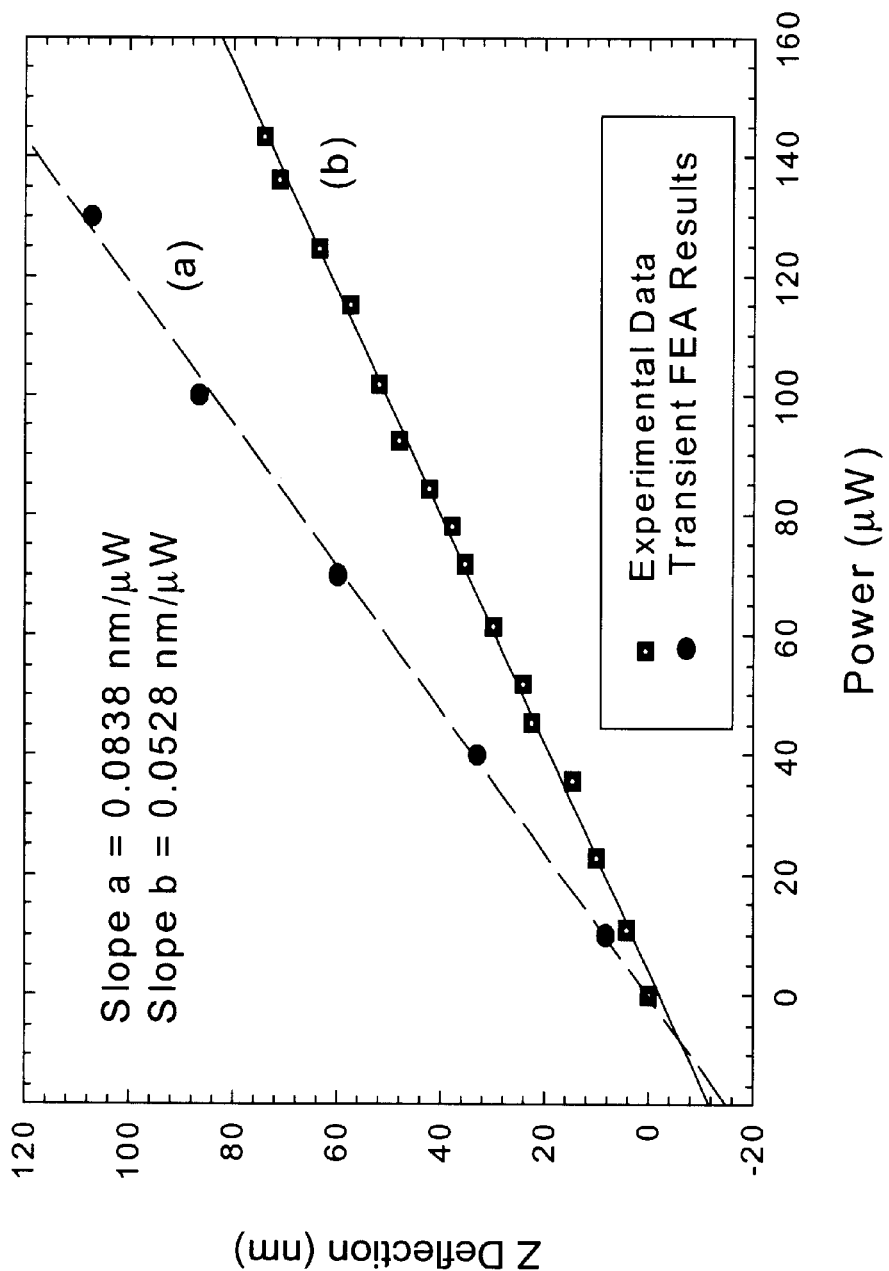
FIG. 5 is a graph of deflection vs. power for both experimental data and the transient finite element analysis (FEA) results for a single side coating.

Assuming a spatially uniform incident power, dQ/dt, onto a bimaterial microcantilever, the maximum deflection depends on the temperature rise and is proportional to the incident power. The thermally induced deflection of the microcantilever is caused by the bimaterial effect which arises due to the difference in the thermal properties of the metal layer and the geometry of the microcantilever. In FIG. 5, we plotted the maximum bending, $z_{max}$, as a function of the absorbed power for a pentalever with a uniform bimetallic coating on a single side, $P_{th}$, and it can be seen that the maximum bending increases linearly with increasing power. The reflectivity of the gold film is >0.99, and the reflectivity was taken into account when determining the absorbed power. From the slope of the line in FIG. 5, we obtained a deflection sensitivity of approximately 0.053 nm/$\mu$W. Using a Stanford Research Systems SR 540 chopper to modulate the IR radiation at a frequency of 30 Hz, we calculated a noise equivalent power (NEP) of 520 pW/Hz$^{1/2}$.

Figure 6:
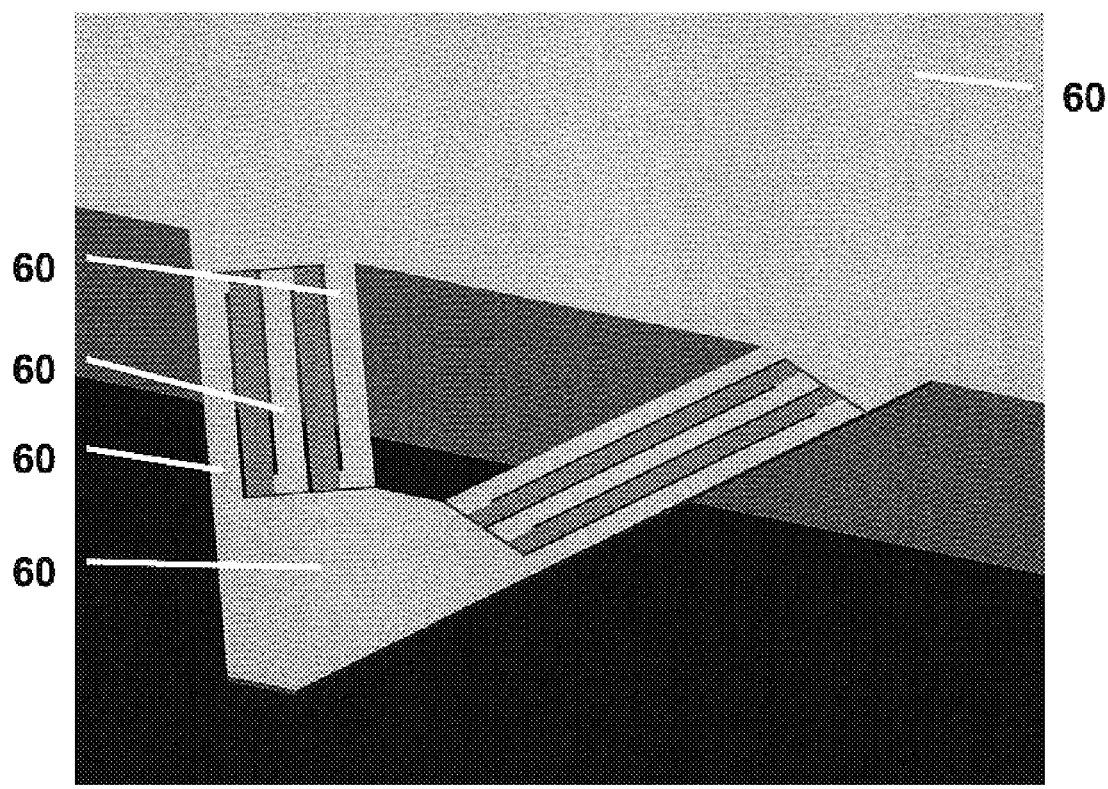
FIG. 6 is the top view of the alternating coated leg segment pentalever of the instant invention with coating applied to the top of the first, third, and fifth segments of each leg, as well as the entire top of the collecting surface.

FIG. 6 is a top view of the alternating coated leg segment pentalever of the instant invention with coating 60 applied to the top of the first, third, and fifth leg segments of each leg, as well as the entire top of the collecting surface.

Figure 7:
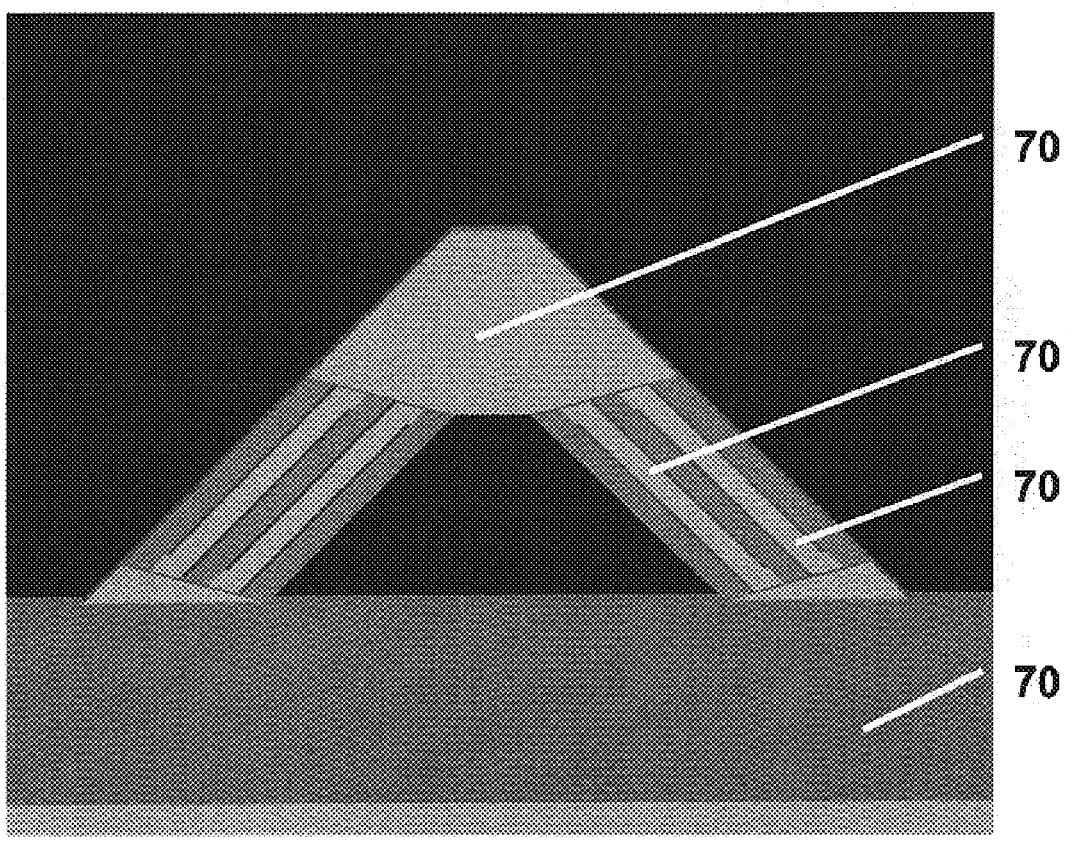
FIG. 7 is a bottom view of the alternating coated leg segment pentalever of the instant invention with coating applied to the bottom of the second and fourth leg segments and the entire bottom of the collecting surface.

FIG. 7 is a bottom view of the alternating coated leg segment pentalever of the instant invention with coating 70 applied to the bottom of the second and fourth leg segments of each leg, as well as the entire bottom of the collecting surface.

The micro-cantilever thermal detector was found to exhibit two distinct thermal response times due to the incoming IR radiation; a time $\tau_{th,1}$<1 ms and a time $\tau_{th,2}$ that is somewhat longer (~10 ms). The fast thermal response is attributed to thermal equilibrium between the top (exposed to the IR radiation) and the bottom surfaces, while the longer thermal response results from the heat flow (along the body of the microcantilever) to the supporting base.

Figure 4:
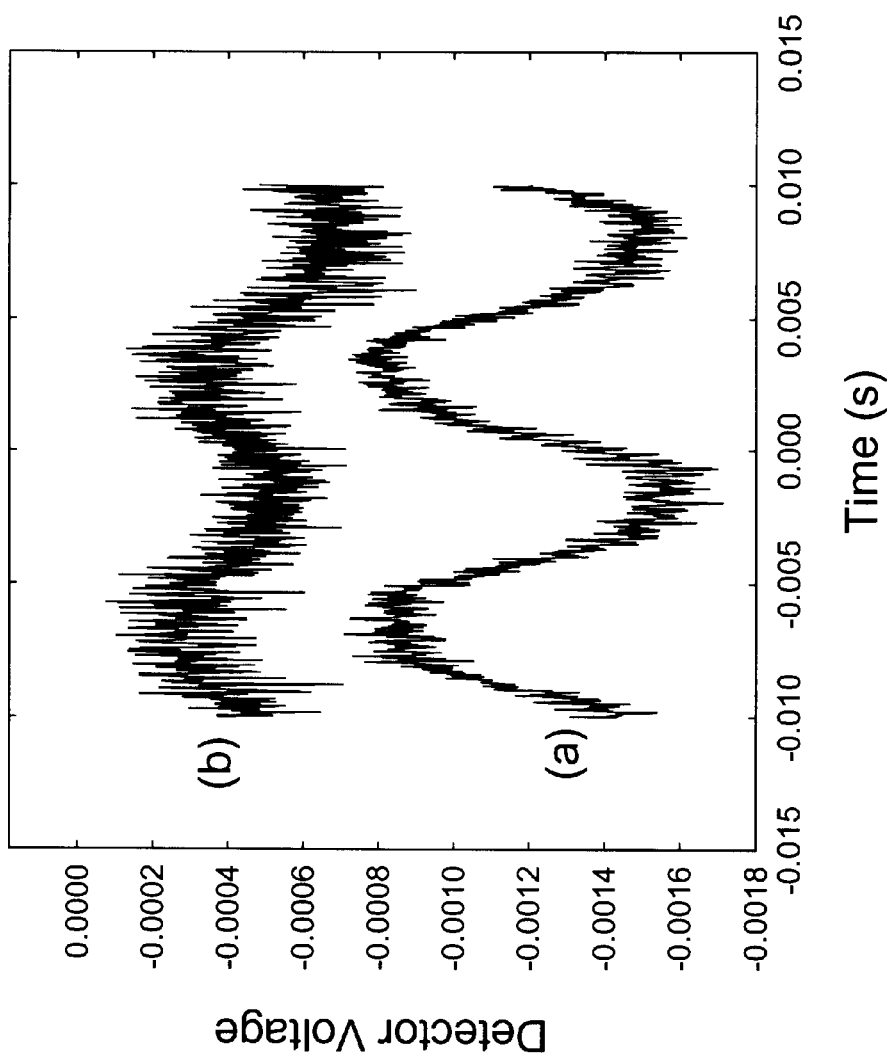
FIG. 4 is a graph of detector voltage vs. time for a single-side coating.

Since the read-out scheme employs laser beam reflection from the microstructure pad, the alternating bimaterial approach has an additional advantage over previous configurations. Since the device pad is metal coated from both sides, there is only a deflection in the supporting leg structure. In previous approaches the pad would also warp from the bimaterial construction and cause a lensing effect. This effect provided some measurement difficulties since it was necessary to compensate for probe beam convergence or divergence. We found nearly a factor of three improvement in response sensitivity for the alternating bimaterial pentalever structure compared to the simple bimaterial pentalever. The experimental results for both of these geometries are shown in FIG. 4 for the alternating coating pentalever (a) of this invention and the bimaterial top coated cantilever (b) of earlier designs. Future direction for achieving greater sensitivity will focus on both material and micromechanical optimizations. The bimaterial effect can be further optimized by selecting polymers instead of metals to work with the silicon substrates. Certain polymers have a factor of four greater coefficients of expansion compared to even zinc. The micro-mechanical structure can be taken to the next logical level to produce a seven legged heptalever device.

The results of the finite element analysis can be used to gain insight into the behavior of the micro-device, and its response to the applied stimulus. The results of the modal analysis can be used to give insight into the expected shape of the device response and an approximation of the responsivity of the device to external stimulus. The normal bending of the device occurs at a fundamental frequency of 12.72 kHz as shown in Table 1. The other modes of the device represent vibrations of the individual legs of the device. FIG. 10 shows the temperature distribution from the thermal analysis. In this figure, it was observed that the greatest temperature was achieved in the "collector" or "pad" area at the end of the device, and the temperature can be seen to decrease along the legs of the device indicating heat transfer through the legs of the device itself. FIG. 9 illustrates the deformed shape of the cantilever due to bimetallic bending. In designing this device, it was anticipated that the thermal deflection would greatly increase as each individual section of the legs deflected, however the model does not show this to be the case. The effect of folding the legs allows the thermal resistance of the device to be increased due to decreased area and increased path length, which increases the deflection of the device due to bimetallic bending.

The results of the optimization study indicate that changing the coating thickness has a tremendous influence on the temperature change of the device and the maximum deflection. The optimum thickness is seen in the peak of the coating thickness versus maximum bending plot shown in FIG. 3. It should be noted that the peak in the displacement versus coating thickness curve occurs due to several of the properties in the gold layer. Although the gold layer has a higher coefficient of thermal expansion than silicon, the gold layer also has a higher thermal conductivity. Therefore as the coating thickness is increased, a limit is reached where the increase in the transport of energy away from the detector negates any benefits from increased coating thickness.

FIG. 5 compares the results of the transient analysis with the experimental results. The sensitivity of the pentalever was determined experimentally to be 0.0528 nm/$\mu$W and determined to be 0.0838 nm/$\mu$W by the analysis. These results are for the pentalever coated only on the top surface.

The improvement in the response seen in the laboratory by alternating the coating was predicted by the finite element analysis. The amount of improvement seen in the lab was slightly less than that predicted, and that may be attributed to differences between the individual cantilevers tested. Direct comparison of these two geometries is difficult, due to the fact that the amount of rotation and displacement of the non-alternating coating cantilever varies significantly along the length of the cantilever.

Simple changes in the geometry of micro-sensors can have significant effects on their response. The effects of varying the bimaterial coating thickness were shown to have drastic effect on the response of the device. The initial FEA of the single-side coated cantilever gave insight as to the necessity to apply the coating to alternating legs of the pentalever. The analysis showed that the alternating coating would solve problems encountered by the "lensing" of the detector surface, provide a pure rotation as opposed to a curling of the detector surface, and deliver a factor of four better response. These results compared well with the factor of three increase in response seen in experimental data.

We claim:

1. A microcantilever thermal detector comprising:
   a substrate having an upper side, lower side, fixed end, and deflective end,
   said substrate having at least one leg interposed between said fixed end and said deflective end,
   said leg comprising at least three essentially parallel leg segments interconnected on alternate opposing ends and aligned in a serpentine pattern with only the first leg segment attached to said fixed end and only the last leg segment attached to said deflective end, wherein a thermal change in said parallel lea segments causes a measurable deflection of the deflective end, which correlates to said thermal change.

2. The microcantilever of claim 1 further comprising an upper coating on said upper side of said substrate.

3. The microcantilever of claim 2 further comprising a lower coating on said lower side of said substrate.

4. The microcantilever of claim 3 wherein said upper coating on each said leg is limited to alternating leg segments.

5. The microcantilever of claim 3 wherein said upper coating is limited to said fixed end and alternating leg segments of each leg.

6. The microcantilever of claim 4 wherein said lower coating on each leg segment is limited to alternating leg segments of each said leg having no upper coating, whereby the deflection of said microcantilever is the combined sum of the deflection of each leg segment.

7. The microcantilever of claim 5 wherein said lower coating is limited to said fixed end and alternating leg segments of each said leg having no upper coating, whereby the deflection of said microcantilever is the combined sum of the deflection of each leg segment.

8. The microcantilever of claim 6 wherein said substrate is selected from the group consisting of silicon and silicon nitride.

9. The microcantilever of claim 7 wherein said substrate is selected from the group consisting of silicon and silicon nitride.

10. The microcantilever of claim 8 wherein said upper coating and said lower coating is selected from the group consisting of gold, platinum, chromium and polymers.

11. The microcantilever of claim 9 wherein said upper coating and said lower coating is selected from the group consisting of gold, platinum, chromium and polymers.

12. The microcantilever of claim 10 wherein said substrate is approximately 1.0 $\mu$m thick.

13. The microcantilever of claim 10 wherein said upper coating and said lower coating is approximately 50 nm thick.

14. The microcantilever of claim 10 wherein the temperature change from said fixed end to said deflective end is at most approximately 0.226 degrees Centigrade.

15. The microcantilever of claim 10 wherein the rotation in the center of the collector area is at least approximately 0.0041 degrees.

16. The microcantilever of claim 10 wherein the deflection sensitivity is at least approximately 0.053 nm/$\mu$W.

17. The microcantilever of claim 10 wherein the noise equivalent power is at least approximately 520 pW/Hz$^{1/2}$.

18. The microcantilever of claim 10 wherein the thermal response time is less than 1 millisecond.

19. The microcantilever of claim 10 wherein the fundamental frequency is approximately 12.72 kHz.

* * * * *